(12) United States Patent
Johnson et al.

(10) Patent No.: US 8,734,445 B2
(45) Date of Patent: May 27, 2014

(54) ELECTROSURGICAL INSTRUMENT WITH SEALING AND DISSECTION MODES AND RELATED METHODS OF USE

(75) Inventors: Kristin D. Johnson, Louisville, CO (US); Scott F. Alexander, Westminster, CO (US)

(73) Assignee: Covidien LP, Mansfield, MA (US)

( * ) Notice: Subject to any disclaimer, the term of this patent is extended or adjusted under 35 U.S.C. 154(b) by 860 days.

(21) Appl. No.: 12/876,705

(22) Filed: Sep. 7, 2010

(65) Prior Publication Data
US 2012/0059374 A1 Mar. 8, 2012

(51) Int. Cl.
*A61B 18/12* (2006.01)
(52) U.S. Cl.
USPC .......................................................... 606/51
(58) Field of Classification Search
USPC ............................. 606/24, 34, 41, 48, 51–52
See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| D348,930 S | 7/1994 | Olson |
| 5,389,104 A | 2/1995 | Hahnen et al. |
| 5,391,166 A | 2/1995 | Eggers |
| 5,403,312 A | 4/1995 | Yates et al. |
| 5,522,830 A | 6/1996 | Aranyi |
| 5,531,744 A | 7/1996 | Nardella et al. |
| 5,549,623 A | 8/1996 | Sharpe et al. |
| D384,413 S | 9/1997 | Zlock et al. |
| 5,913,857 A | 6/1999 | Ritchart et al. |
| 5,913,866 A | 6/1999 | Ginn et al. |
| 5,976,132 A * | 11/1999 | Morris .............................. 606/49 |
| 6,024,744 A | 2/2000 | Kese |
| D424,694 S | 5/2000 | Tetzlaff et al. |
| D425,201 S | 5/2000 | Tetzlaff et al. |
| 6,066,137 A * | 5/2000 | Greep .............................. 606/45 |
| 6,102,909 A * | 8/2000 | Chen et al. ....................... 606/45 |
| 6,206,877 B1 | 3/2001 | Kese |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

European Search Report for European Application No. 11180368.0 dated Feb. 24, 2012.

(Continued)

*Primary Examiner* — Michael Peffley
*Assistant Examiner* — Daniel Fowler

(57) ABSTRACT

An end effector assembly is provided. The end effector assembly includes a pair of first and second jaw members including respective seal plates adapted to connect to a source of electrosurgical energy. The first and second jaw members operable in a first bipolar mode of operation for treating tissue and a second bipolar mode of operation for separating tissue. A dissector translatable through one of the first and second jaw members is in electrical communication with one of the seal plates of the first and second jaw members and activatable in the second bipolar mode of operation for separating tissue when the first and second jaw members are in one of the open and clamping position and tissue is adjacent thereto.

10 Claims, 4 Drawing Sheets

(56) References Cited

U.S. PATENT DOCUMENTS

| | | |
|---|---|---|
| D449,886 S | 10/2001 | Tetzlaff et al. |
| D457,958 S | 5/2002 | Dycus et al. |
| D457,959 S | 5/2002 | Tetzlaff et al. |
| 6,423,080 B1 | 7/2002 | Gellman et al. |
| 6,425,896 B1* | 7/2002 | Baltschun et al. ............ 606/51 |
| 6,458,128 B1 | 10/2002 | Schulze |
| 6,464,702 B2 | 10/2002 | Schulze et al. |
| 6,500,176 B1* | 12/2002 | Truckai et al. ............... 606/51 |
| 6,679,882 B1* | 1/2004 | Kornerup ...................... 606/51 |
| 6,695,840 B2 | 2/2004 | Schulze |
| 6,736,813 B2 | 5/2004 | Yamauchi |
| 6,752,814 B2 | 6/2004 | Gellman et al. |
| D493,888 S | 8/2004 | Reschke |
| 6,773,434 B2* | 8/2004 | Ciarrocca ...................... 606/51 |
| D496,997 S | 10/2004 | Dycus et al. |
| D499,181 S | 11/2004 | Dycus et al. |
| D509,297 S | 9/2005 | Wells |
| 6,960,210 B2* | 11/2005 | Lands et al. ................... 606/50 |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al |
| 7,270,664 B2 | 9/2007 | Johnson et al. |
| 7,276,068 B2 | 10/2007 | Johnson et al. |
| D564,662 S | 3/2008 | Moses et al. |
| D567,943 S | 4/2008 | Moses et al. |
| 7,381,209 B2 | 6/2008 | Truckai et al. |
| D575,395 S | 8/2008 | Hushka |
| D575,401 S | 8/2008 | Hixson et al. |
| 7,614,999 B2 | 11/2009 | Gellman et al. |
| 7,662,164 B2 | 2/2010 | Kasahara et al. |
| 7,717,914 B2 | 5/2010 | Kimura |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,918,848 B2 | 4/2011 | Lau |
| 2002/0188294 A1* | 12/2002 | Couture et al. ................ 606/51 |
| 2003/0018332 A1 | 1/2003 | Schmaltz et al. |
| 2004/0204734 A1 | 10/2004 | Wagner et al. |
| 2005/0113827 A1* | 5/2005 | Dumbauld et al. ........... 606/45 |
| 2005/0171533 A1* | 8/2005 | Latterell et al. ............... 606/48 |
| 2006/0074417 A1* | 4/2006 | Cunningham et al. ........ 606/51 |
| 2006/0189980 A1* | 8/2006 | Johnson et al. ............... 606/51 |
| 2008/0015567 A1* | 1/2008 | Kimura ........................... 606/41 |
| 2008/0021450 A1* | 1/2008 | Couture .......................... 606/51 |
| 2009/0326530 A1* | 12/2009 | Orban et al. ................... 606/51 |
| 2010/0198248 A1 | 8/2010 | Vakharia |
| 2010/0204697 A1 | 8/2010 | Dumbauld et al. |
| 2010/0204698 A1 | 8/2010 | Chapman et al. |
| 2010/0217258 A1 | 8/2010 | Floume et al. |
| 2010/0249769 A1 | 9/2010 | Nau, Jr. et al. |
| 2010/0249776 A1 | 9/2010 | Kerr |
| 2011/0257643 A1 | 10/2011 | Lau |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026 179 | 12/2005 |
| DE | 20 2007 009317 | 10/2007 |
| DE | 19738457 | 1/2009 |
| EP | 0913126 | 5/1999 |
| EP | 1159926 | 12/2001 |
| EP | 1878400 | 1/2008 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/110264 | 11/2005 |

OTHER PUBLICATIONS

European Search Report for European Application No. 11180368.0 dated Dec. 2, 2011.
U.S. Appl. No. 09/387,883, filed Sep. 1, 1999.
U.S. Appl. No. 09/591,328, filed Jun. 9, 2000.
U.S. Appl. No. 12/336,970, filed Dec. 17, 2008.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/535,869, filed Aug. 5, 2009.
U.S. Appl. No. 12/543,831, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/568,838, filed Sep. 29, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
U.S. Appl. No. 12/619,100, filed Nov. 16, 2009.
U.S. Appl. No. 12/692,414, filed Jan. 22, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
U.S. Appl. No. 12/757,340, filed Apr. 9, 2010.
U.S. Appl. No. 12/758,524, filed Apr. 12, 2010.
U.S. Appl. No. 12/759,551, filed Apr. 13, 2010.
U.S. Appl. No. 12/769,444, filed Apr. 28, 2010.
U.S. Appl. No. 12/770,369, filed Apr. 29, 2010.
U.S. Appl. No. 12/770,380, filed Apr. 29, 2010.

(56) References Cited

OTHER PUBLICATIONS

U.S. Appl. No. 12/770,387, filed Apr. 29, 2010.
U.S. Appl. No. 12/773,526, filed May 4, 2010.
U.S. Appl. No. 12/773,644, filed May 4, 2010.
U.S. Appl. No. 12/775,553, filed May 7, 2010.
U.S. Appl. No. 12/786,589, filed May 25, 2010.
U.S. Appl. No. 12/791,112, filed Jun. 1, 2010.
U.S. Appl. No. 12/792,001, filed Jun. 2, 2010.
U.S. Appl. No. 12/792,008, filed Jun. 2, 2010.
U.S. Appl. No. 12/792,019, filed Jun. 2, 2010.
U.S. Appl. No. 12/792,038, filed Jun. 2, 2010.
U.S. Appl. No. 12/792,051, filed Jun. 2, 2010.
U.S. Appl. No. 12/792,068, filed Jun. 2, 2010.
U.S. Appl. No. 12/792,097, filed Jun. 2, 2010.
U.S. Appl. No. 12/792,262, filed Jun. 2, 2010.
U.S. Appl. No. 12/792,299, filed Jun. 2, 2010.
U.S. Appl. No. 12/792,330, filed Jun. 2, 2010.
U.S. Appl. No. 12/820,024, filed Jun. 23, 2010.
U.S. Appl. No. 12/821,253, filed Jun. 23, 2010.
U.S. Appl. No. 12/832,772, filed Jul. 8, 2010.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" , Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.

(56) References Cited

OTHER PUBLICATIONS

Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

ELECTROSURGICAL INSTRUMENT WITH SEALING AND DISSECTION MODES AND RELATED METHODS OF USE

BACKGROUND

1. Technical Field

The present disclosure relates to an electrosurgical instrument and, more particularly, to an electrosurgical instrument configured to dissect, seal or otherwise treat tissue.

2. Background of Related Art

Electrosurgical instruments, e.g., electrosurgical forceps (open or closed type), are well known in the medical arts and typically include an end effector assembly including jaw members configured to manipulate tissue (e.g., grasp and seal tissue). Typically, the electrosurgical forceps utilizes both mechanical clamping action and electrical energy to effect hemostasis by heating the tissue and blood vessels to coagulate, cauterize, seal, desiccate, and/or fulgurate tissue.

In certain instances, it may prove advantageous to cut or dissect tissue that has been electrosurgically treated, e.g., sealed. In such instances, a cutting element, e.g., a knife blade, may be configured to translate through a knife channel that is disposed on one or both of the jaw members. Typically, the knife blade is manufactured from surgical steel that is generally very expensive. Moreover, the surgical steel typically needs to be machined into thin sheets and, subsequently, cut or formed into desired shapes and/or dimensions. As can be appreciated, incorporating the knife blade into the electrosurgical instrument may increase manufacturing costs of the electrosurgical instrument.

In addition to electrosurgical instruments, ultrasonic instruments may be utilized to treat tissue. Conventional ultrasonic instruments, e.g., ultrasonic dissectors, typically, include a housing, a handle assembly, a shaft having a transducer and/or a waveguide, and an end effector assembly attached to a distal end of the shaft. The end effector includes jaw members configured to manipulate tissue (e.g., grasp and seal tissue). Typically, ultrasonic dissectors utilize both mechanical clamping action and ultrasonic energy to effect hemostasis by heating the tissue and blood vessels to coagulate, cauterize, seal, cut, dissect, desiccate, and/or fulgurate tissue. While ultrasonic instruments may effectively treat and, subsequently, dissect tissue, ultrasonic instruments are typically not configured to articulate and/or "flex." That is, the transducer and/or waveguide that are disposed within the shaft, typically, are not flexible and, thus, limit or eliminate the degree of flexibility of the shaft. As can be appreciated, this limits the use of the ultrasonic dissectors in the surgical environment.

SUMMARY

The present disclosure provides an end effector assembly. The end effector assembly has a pair of first and second jaw members including respective seal plates adapted to connect to a source of electrosurgical energy. One or both of the first and second jaw members may be movable relative to the other jaw member from an open position, wherein the first and the second jaw members are disposed in spaced relation relative to one another, to a clamping position, wherein the first and second jaw members cooperate to grasp tissue therebetween. The first and second jaw members are operable in two bipolar modes of operation, a first bipolar mode of operation for treating tissue and a second bipolar mode of operation for separating tissue. A dissector translatable through one or both of the first and second jaw members is in electrical communication with one of the seal plates of the first and second jaw members and activatable in the second bipolar mode of operation for separating tissue when the first and second jaw members are in one of the open and clamping position and tissue is adjacent thereto.

The present disclosure provides a system for performing an electrosurgical procedure. The system includes a source of electrosurgical energy configured to operate in two or more bipolar modes of operation, a first bipolar mode of operation for treating tissue and a second bipolar mode of operation for separating tissue. The system includes an electrosurgical forceps that includes a handle having one or more shafts extending therefrom and defining a longitudinal axis therethrough. An end effector assembly operatively connected to a distal end of the shaft and has a pair of first and second jaw members including respective seal plates adapted to connect to a source of electrosurgical energy. One or both of the first and second jaw members are movable relative to the other jaw member from an open position, wherein the first and the second jaw members are disposed in spaced relation relative to one another, to a clamping position, wherein the first and second jaw members cooperate to grasp tissue therebetween. The first and second jaw members are operable in two bipolar modes of operation, a first bipolar mode of operation for treating tissue and a second bipolar mode of operation for separating tissue. A dissector translatable through one or both of the first and second jaw members is in electrical communication with one of the seal plates of the first and second jaw members and activatable in the second bipolar mode of operation for separating tissue when the first and second jaw members are in one of the open and clamping position and tissue is adjacent thereto.

The present disclosure also provides a method for performing an electrosurgical procedure. The method includes positioning tissue between first and second jaw members of an electrosurgical instrument. The first and second jaw members including respective seal plates that are adapted to connect to a source of electrosurgical energy. The first and second jaw members are operable in two bipolar modes of operation, a first bipolar mode of operation for treating tissue and a second bipolar mode of operation for separating tissue. A dissector translatable through one or both of the first and second jaw members is in electrical communication with one of the seal plates of the first and second jaw members and is activatable in the second bipolar mode of operation for separating tissue when the first and second jaw members are in one of the open and clamping position and tissue is adjacent thereto. The method includes closing the first and second jaw members such that the tissue is clamped therebetween. Transmitting electrosurgical energy in the first bipolar mode of operation to the first and second jaw members for electrosurgically treating tissue is a step of the method. A step of the method includes translating the dissector through a channel that is operably disposed on one or both of the first and second jaw members. And, transmitting electrosurgical energy in the second bipolar mode of operation to the jaw member with the dissector for dissecting the electrosurgically treated tissue is another step of the method.

BRIEF DESCRIPTION OF THE DRAWINGS

Embodiments of the presently disclosed specimen retrieval apparatus are described hereinbelow with reference to the drawings wherein.

DETAILED DESCRIPTION OF THE EMBODIMENTS

Figure 1:
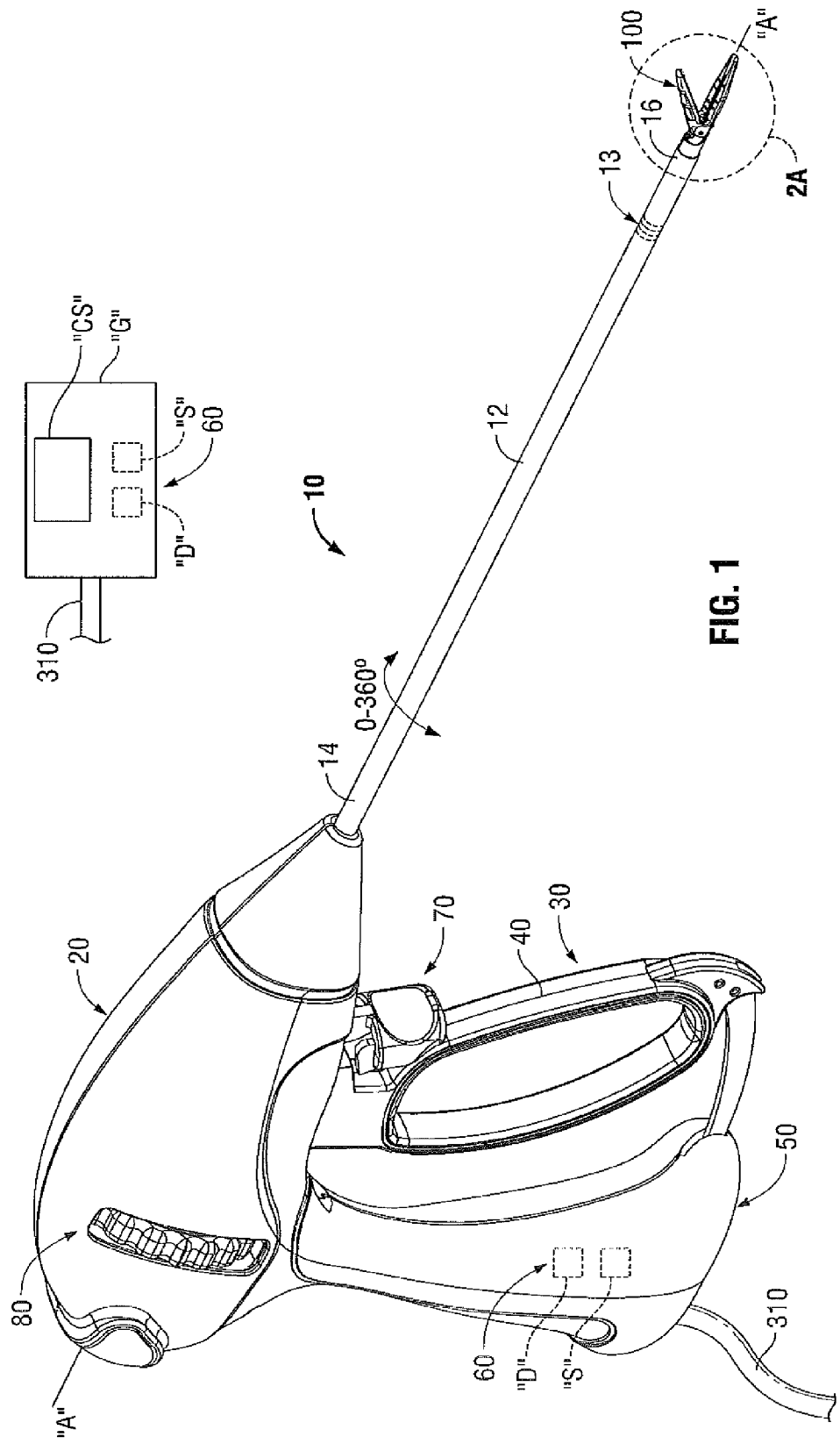
FIG. 1 is a left, perspective view of an electrosurgical instrument including an end effector having jaw members according to an embodiment of the present disclosure.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, will refer to the end of the forceps 10 which is closer to the user, while the term "distal" will refer to the end that is farther from the user.

Figure 2A:
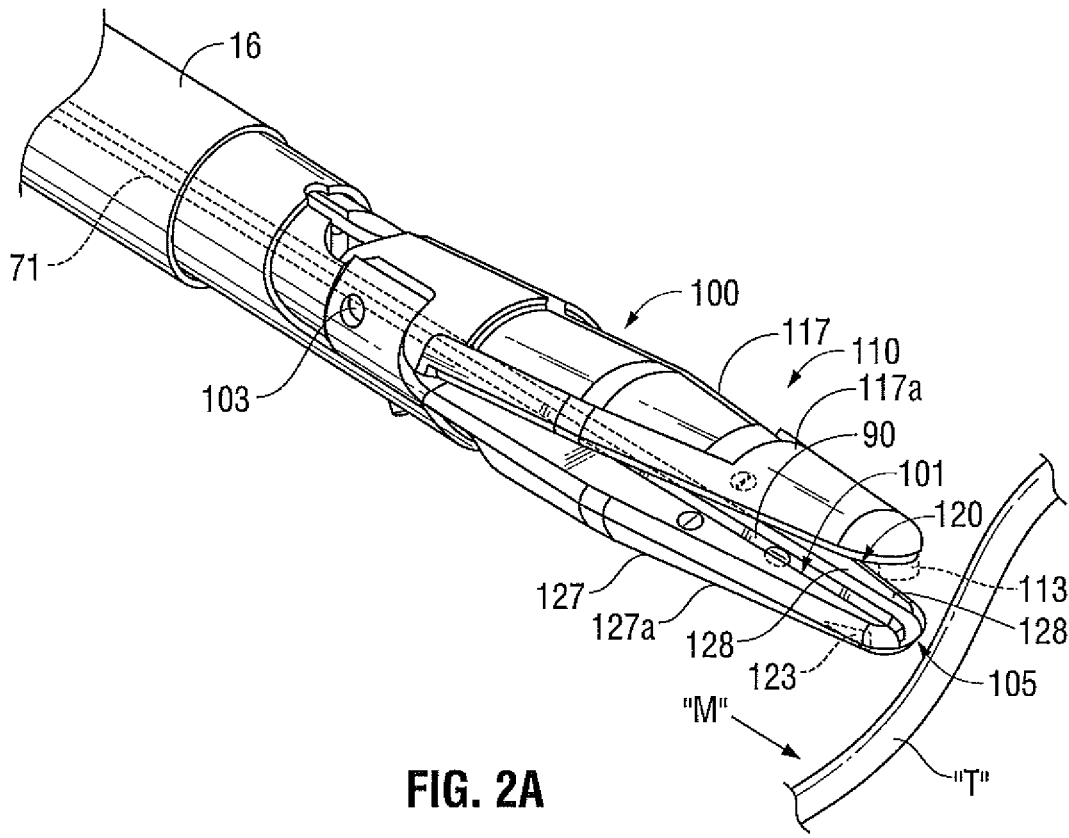
FIG. 2A is an enlarged, left, perspective view of the indicated area of detail of FIG. 1 with an electrical dissecting member (dissector) in a partially extended position.
Figure 2B:
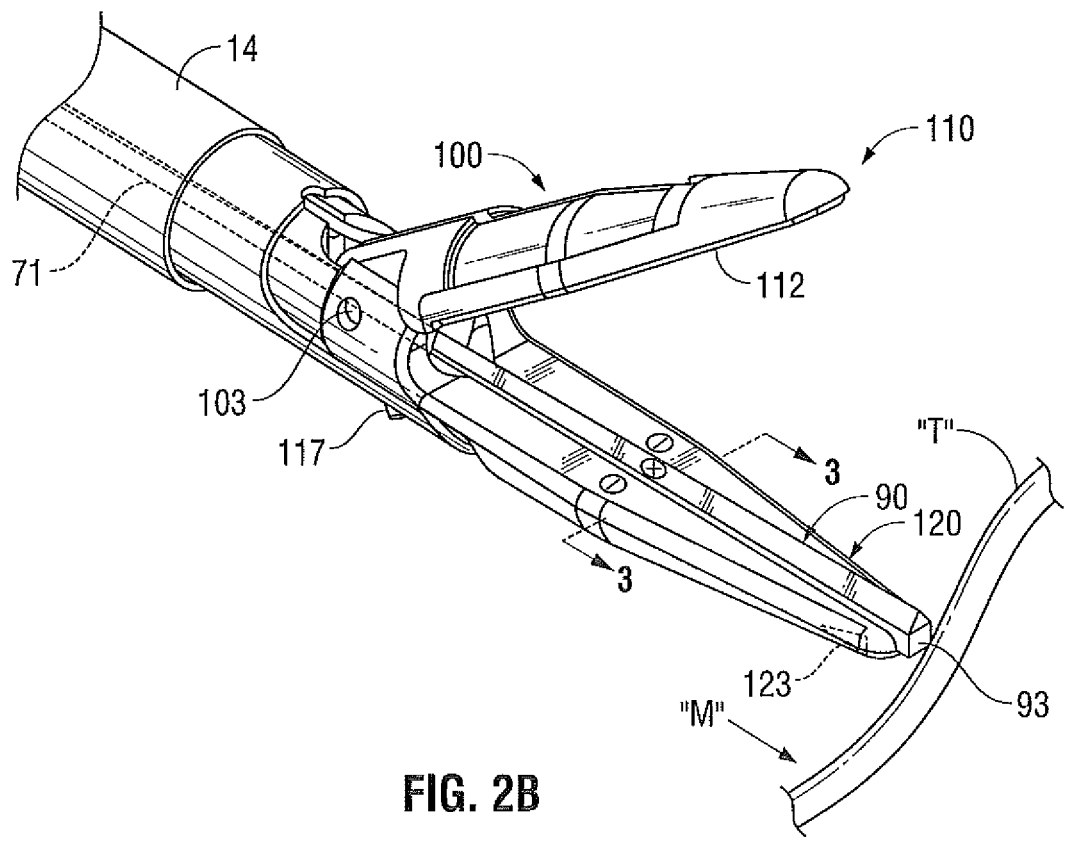
FIG. 2B is a left, perspective view with the dissector depicted in FIG. 2A in a fully extended position.
Figure 3:
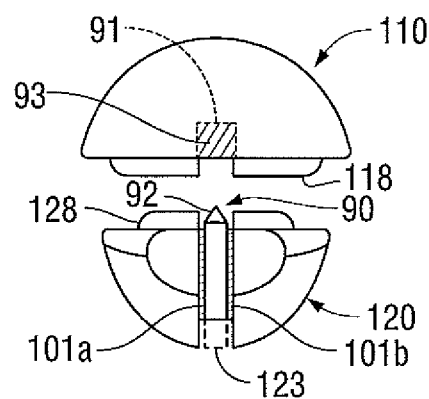
FIG. 3 is a cut-away view taken along line segment "3-3" in FIG. 2B.

Turning now to FIGS. 1-3, and initially with reference to FIG. 1 an electrosurgical instrument, e.g., an electrosurgical forceps 10 (forceps 10), that includes an end effector 100 according to an embodiment of the present disclosure is shown. Forceps 10 operatively and selectively couples to an electrosurgical generator (generator "G") for performing an electrosurgical procedure (FIG. 1). For purposes herein, an electrosurgical procedure may include sealing, cutting, dissecting, cauterizing, coagulating, desiccating, and fulgurating tissue all of which may employ RF energy. The generator "G" is configured for one or more bipolar modes of operation and/or monopolar operation. The generator "G" may include or is in operative communication with a control system "CS" (FIG. 1) that may include one or more processors in operative communication with one or more control modules that are executable on the processor. The control module not explicitly shown) may be configured to instruct one or more modules to transmit electrosurgical energy, which may be in the form of a wave or signal/pulse, via one or more cables (e.g., a cable 310) to one or both jaw members 110 and 120 of an end effector 100.

Continuing with reference to FIG. 1, forceps 10 is configured for use with various surgical procedures and includes a housing 20, a shaft 12, a handle assembly 30, a rotating assembly 80, a trigger assembly 70 and an end effector 100.

Housing 20 is configured to house and/or support one or more components associated with the forceps 10, such as, for example, a drive assembly (not shown), rotating assembly 80, handle assembly 30 and trigger assembly 70. A distal end of the housing 20 supports the shaft 12.

Shaft 12 extends distally from the housing 20 and defines a longitudinal axis "A-A" therethrough (FIG. 1). The shaft has a distal end 16 configured to mechanically engage the end effector assembly 100 and a proximal end 14 that mechanically engages the housing 20 (FIG. 1). In certain instances, the shaft 12 may be configured to bend or articulate. For example, shaft 12 may be resilient or portion thereof may include an articulating member 13 (shown in phantom in FIG. 1).

Handle assembly 30 includes a fixed handle 50 and a movable handle 40 (FIG. 1). Fixed handle 50 is integrally associated with housing 20 and handle 40 is movable relative to fixed handle 50. In certain embodiments, movable handle 40 of handle assembly 30 may be operably coupled to the drive assembly, which together may be configured to cooperate to impart movement of one or both of jaw members 110 and 120 to move from an open position, wherein the jaw members 110 and 120 are disposed in spaced relation relative to one another, to a clamping or closed position, wherein the jaw members 110 and 120 cooperate to grasp tissue therebetween.

Rotating assembly 80 is configured to rotate the shaft 12 including the jaw members 110 and 120 in either a clockwise or counter-clockwise direction that ranges from about 0-360° (FIG. 1).

Trigger assembly 70 is operably coupled to an electrical cutting element or dissection member 90 (hereinafter dissector 90) and is configured to translate the dissector 90 proximally and distally through a dissector channel 101 (FIG. 2A) that is operably disposed on one or both of the jaw members 110 and 120. Dissector element is illustrated operably disposed in jaw member 120.

Although the figure drawings depict a forceps 10 for use in connection with endoscopic surgical procedures, the present disclosure may be used for more traditional open surgical procedures. The open version of the forceps may also include the same or similar operating components and features as described below.

For a more detailed description of the housing 20, shaft 12, handle assembly 30 (including movable and fixed handles 40 and 50, respectively), rotating assembly 80, trigger assembly 70 and electrosurgical cable 310 (including line-feed configurations and/or connections), reference is made to commonly owned U.S. Pat. No. 7,150,097 to Sremcich filed Jun. 13, 2003.

With reference again to FIG. 1, one or more buttons or switches 60 are operably disposed on the forceps 10. More particularly, and in the illustrated embodiment, two switches "D" and "S" are shown operably disposed on the fixed handle 50. In certain embodiments, it may prove advantageous to provide the switches 60 on the generator "G," see FIG. 1, for example. This of course will depend on the contemplated uses of a manufacturer. Switches "D" and "S" are in operative communication with the generator "G" and/or control system "CS" and are configured to place the forceps 10 in one or more modes of operation. More particularly, switch "S" is configured to place the forceps 10 in a first bipolar mode of operation for treating tissue, e.g., sealing tissue, and switch "D" is configured to place the forceps 10 in a second bipolar mode of operation for separating tissue, e.g., dissecting tissue.

In the first bipolar mode of operation the generator "G" including control system "CS" and the forceps 10 are configured to fuse, seal, coagulate and/or fulgurate tissue. To this end, in the first bipolar mode of operation, the respective seal plates 118 and 128 of jaw members 110 and 120 are both active, include opposing polarities and are configured to transmit electrosurgical energy, e.g., current, therebetween. In the second bipolar mode of operation, the generator "G" including control system "CS" and the forceps 10 are configured to dissect, cut, sever and/or transect tissue. To this end, in the second bipolar mode of operation, seal plate 128 is active, dissector 90 is active, seal plate 118 is inactive or neutral (and/or is highly resistive to current flow), and seal plate 128 including dissector 90 is configured to transmit electrosurgical energy, e.g., current, to tissue.

A translation bar or flexible band 71 (shown in phantom in FIGS. 2A and 2B) is operably coupled to the trigger assembly 70 and is configured to translate the dissector 90 distally and proximally when the trigger assembly 70 is pressed and released, respectively. Translation band 71 operably couples to the dissection member 90 by any suitable coupling methods. In the illustrated embodiment, the dissection member 90 is welded to the translation band 71.

With reference to FIGS. 2A and 2B, an embodiment of end effector assembly 100 including jaw members 110 and 120 is illustrated. In the illustrated embodiment, jaw members 110 and 120 are of the unilateral type. That is, jaw member 110 is movable, e.g., pivotable, with respect to jaw member 120. Alternatively, jaw members 110 and 120 may be of the bilateral type. That is, each of the jaw members 110 and 120 are movable with respect to each other. To facilitate pivoting the jaw member 110 with respect to jaw member 120, a pivot pin 103 couples the jaw members 110 and 120 to the distal end 16 of the shaft 12, FIGS. 2A and 2B. Jaw members 110 and 120, and operative components associated therewith, may be formed from any suitable material, including but not limited to metal, metal alloys, plastic, plastic composites, and so forth.

Continuing with reference to FIGS. 2A and 2B, jaw member 110 is shown including a jaw housing 117. Electrically conductive seal plate 118 is operably supported on and secured to jaw housing 117. More particularly, a distal end 117a of jaw member 110 may be configured to securely engage the electrically conductive seal plate 118 or, with respect to a monolithic jaw member, form the seal plate 118.

Figure 6:
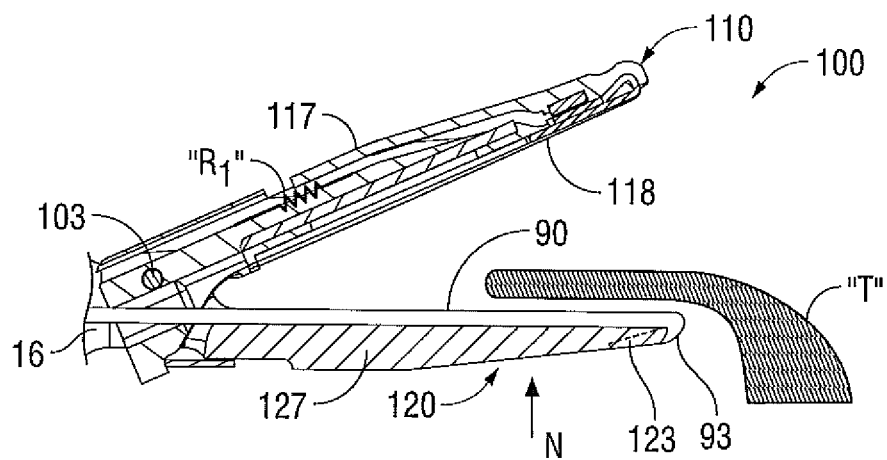
FIG. 6 is a side view of jaw members depicted in FIGS. 2A and 2B with tissue positioned across the dissector.
Figure 7:
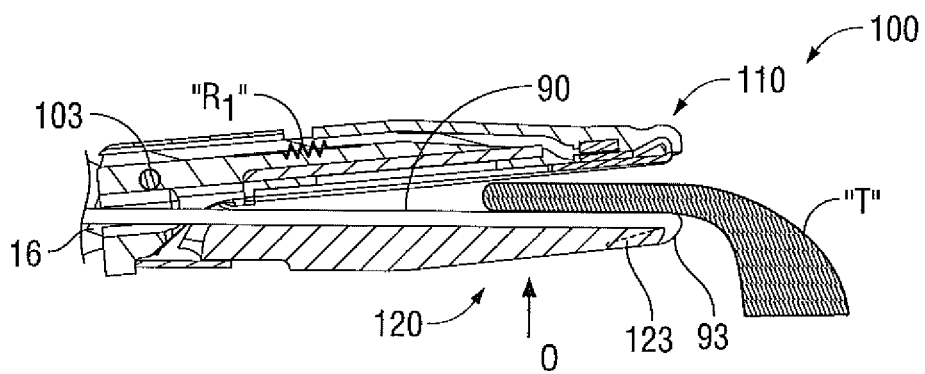
FIG. 7 is a side view of jaw members depicted in FIGS. 2A and 2B with tissue positioned across the dissector with the jaw members in a clamping position.

As noted above, in the second bipolar mode of operation, seal plate 118 is inactive or neutral (and/or is highly resistive to current flow). To this end, a high impedance resistor "R1" may be included in the circuitry of the jaw member 110 and placed in-line between the seal plate 118 and the return path to the generator "G" to allow minimal current to return through the seal plate 118. For illustrative purposes, the high impedance resistor is shown disposed within the jaw housing 117 of the jaw member 110 (FIGS. 6 and 7). Placing the high impedance resistor "R1" in-line between the seal plate 118 and the return path to the generator "G" diminishes or eliminates the likelihood of the seal plate 118 shorting during operation of the forceps 10 in the second bipolar mode of operation.

Similar to jaw member 110, jaw member 120 includes a jaw housing 127 having a distal end 127a that is configured to support seal plate 128 (FIGS. 2A and 2B).

In the illustrated embodiment, and to facilitate separating tissue during the second bipolar mode of operation, the jaw member 120 including the seal plate 128 includes a width that is smaller in comparison to the width of the jaw member 110 including the seal plate 118. That is, the jaw member 120 including the seal plate 128 is smaller or "finer" than the jaw member 110 including the seal plate 118, see FIG. 3 for example. In accordance with an embodiment of the present disclosure, seal plate 118 of the jaw member 110 (the larger jaw) includes a width that is approximately 1 mm to 2 mm larger than the width of the seal plate of the jaw member 120 (the smaller or "finer" jaw member). Keeping the width of the seal plate of the jaw member 120 1 mm to 2 mm smaller than the width of the seal plate of the jaw member 110 improves visualization and dissection capabilities for the end user, e.g., a surgeon, while maintaining grasping capabilities. In the illustrated embodiment, seal plate of the jaw member 120 includes a width that ranges from about 1 mm to about 3.4 mm and seal plate 118 of the jaw member 120 includes a width that ranges from about 3.5 mm to about 5 mm.

Figure 5:
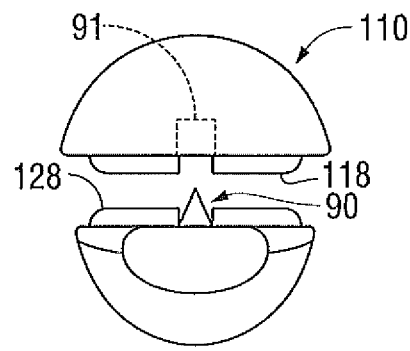
FIG. 5 is a cut-away view of a dissector according to another embodiment of the present disclosure.

In certain embodiments, it may prove advantageous for the jaw members 110 and 120 and/or respective seal plates 118 and 128 to have the same widths (FIG. 5). The specific widths of the jaw members 110 and 120 may depend on factors that include the specific type of surgical procedure including the type of tissue that is to be treated, etc.

In the embodiment illustrated in FIGS. 1-4B, dissector 90 is configured to translate longitudinally through the jaw member 120. To this end, jaw member 120 includes the dissector channel 101 that is configured to receive the dissector when the trigger assembly 70 is actuated.

Dissector channel 101 extends the length of the jaw member 120. Dissector channel 101 is defined by two non-conductive interior walls 101a and 101b (FIG. 3) that substantially surround the dissector 90 when the dissector 90 is translated through the dissector channel 101. Dissector channel 101 may be formed in the seal plate 128 by any suitable methods. In one particular embodiment, the dissector channel 101 is machined or etched into the seal plate 128 during a manufacturing process thereof. In the illustrated embodiment, the two non-conductive interior walls 101a and 101b are coated with a non-conductive material such as, for example, plastic or ceramic. Providing the dissector channel 101 with two non-conductive interior walls 101a and 101b facilitates directing current flow from the dissector 90 to the seal plate 128 (and vice versa) when the forceps 10 is operating in the second bipolar mode of operation.

The dissector channel 101 is configured to accommodate proximal and distal translation of the dissector 90 therein when the forceps 10 is in the second bipolar mode of operation and when the trigger assembly 70 is depressed. To facilitate translation of the dissector 90 within the dissector channel 101, one or both of the dissector 90 and dissector channel 101 including interior walls 101a and 101b may coated with a material or substance that is lubricious, e.g., polytetrafluoroethylene (PTFE). In the illustrated embodiments, the dissector 90 is coated with PTFE. Coating the dissector 90 with PTFE also facilitates preventing tissue from sticking to the dissector 90 after tissue has been electrosurgically treated, e.g., dissected.

Dissector channel 101 may be also configured to raise or elevate the dissector 90 above the seal surface of the seal plate 128 when the dissector 90 is translated distally. To this end, a bottom surface of the dissector channel 101 may be sloped, angled or otherwise configured to raise or elevate the dissector 90 above the seal surface of the seal plate 128. In the illustrated embodiment, one or more protrusions 123 (detents or the like) of suitable dimensions are operably positioned at a distal end of the dissector channel 101 (FIGS. 2A and 2B).

Protrusion 123 includes a generally rectangular configuration with a sloped trailing edge that is angled to provide a smooth transition from the bottom surface of the dissector channel 101 to a leading edge of protrusion 123 such that the dissector 90 is raised a predetermined distance above the seal surface of the seal plate. In the illustrated embodiment, the protrusion 123 is configured to raise the dissector 90 (or portion thereof, e.g., a proximal surface 92) approximately 0.5 mm to 1.0 mm above the seal surface of the seal plate 128.

In certain embodiments, forceps 10 may be configured to dissect into a plane of the electrosurgically treated tissue. In this instance, a distal tip 93 of the dissector 90 may be configured to extend to or slightly past (approximately 0.5 mm to about 1.5 mm) a distal tip of the jaw member 128. With this purpose in mind, the dissector channel 101 extends the length of the jaw member 120 and forms an opening 105 of suitable dimensions at a distal end thereof, as best seen in FIG. 2A. As can be appreciated, in certain instances, it may prove advantageous to have the dissector channel 101 with a closed distal end; this of course will depend on the contemplated uses of a manufacturer, a specific type of surgical procedure including the specific type of tissue to be treated, etc.

Figure 4A:
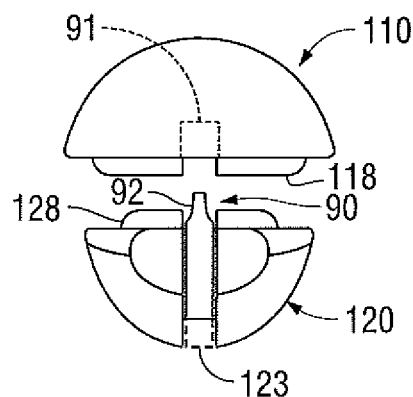
FIGS. 4A-4B are front views illustrating various configurations of the dissector depicted in FIGS. 1-3.
Figure 4B:
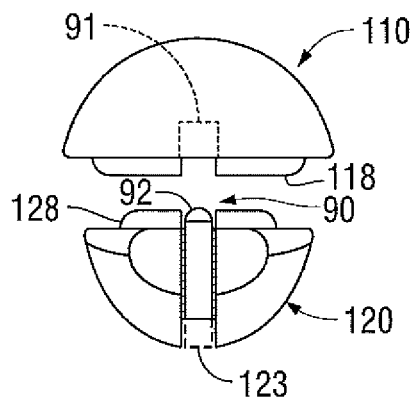

Dissector 90 is configured to separate tissue, e.g., dissect tissue, when the jaw members 110 and 120 are in either the open position (FIGS. 1, 2B and 6) or the closed position (FIG. 7) and when tissue is positioned adjacent thereto. More particularly, and in one particular embodiment, when switch "D" is activated, the forceps 10 is configured to operate in the second bipolar mode of operation. In the second mode of operation, the generator "G" transmits electrosurgical energy to the seal plate 128 and to the dissector 90 such that a user may dissect tissue that has been electrosurgically treated. With this purpose in mind, dissector 90 includes a generally elongated configuration including a proximal surface 92 that is configured to translate through the dissector channel 101. Proximal surface 92 is configured to concentrate current density thereabout when the forceps 10 is in the second bipolar mode of operation. In one particular embodiment, the proximal surface 92 may be configured to maximize current density at the dissector 90. In this instance, the proximal surface 92 may include a triangular cross-sectional configuration with a tip that is pointed (FIGS. 2A-3) or multiple pointed tips (FIG. 4A). Alternatively, and in the instance where current density is not particularly important, i.e., minimal current density at the dissector 90 is desired, proximal surface 92 may include a generally arcuate cross-sectional configuration with a tip that is blunt (see FIG. 4B for example). The specific tip configuration of the proximal surface 92 will depend on one or more factors such as, for example, the specific type of surgical procedure that is to be performed, the type of tissue that is to be treated, the desired power output that is desired at the dissector 90, etc.

Dissector 90 is movable from a partially extended position within the dissector channel 101 (FIG. 2A), to a fully extended position within the dissector channel 101 (FIG. 2B). As noted above, in the fully extended position, the distal tip 93 may extend past the opening 105. In the partially extended position, the dissector 90 is flush with a seal surface of the seal plate 128, and the dissector 90 and the seal plate 128 have the same polarity (FIG. 2A). In the fully extended position, the dissector 90 is elevated from the seal surface of the seal plate 128 and the dissector 90 and the seal plate 128 have a different polarity (FIG. 2B).

In the first bipolar mode of operation, the dissector 90 is flush with the seal surface of seal plate 128, each of the seal plates 118 and 128 is active including the dissector 90 and electrosurgical energy is transmitted from seal plate 128 to seal plate 118. In the second bipolar mode of operation, the dissector 90 is elevated from the seal surface of the seal plate 128, the seal plate 128 is active and electrosurgical energy is transmitted therefrom to the dissector 90 and vice-versa.

Operation of forceps 10 is described in terms of use of a method for electrosurgically treating tissue, such as, for example, during a hysterectomy, a colectomy and/or a Nissen fundoplication, commonly referred to in the art as a lap Nissen. Initially, the forceps 10 is inserted through an incision in a patient. Tissue is positioned between the jaw members 110 and 120. In the instance where a user wants to seal tissue, the user activates switch "S." Activation of switch "S" indicates to the generator "G" and/or control system "CS" that the jaw members 110 and 120 are ready to operate in the first bipolar mode of operation. Thereafter, generator "G" delivers electrosurgical energy to the respective seal plates 118 and 128 of the jaw members 110 and 120 to seal tissue positioned between the jaw members 110 and 120.

To dissect tissue, a user activates switch "D." Activation of switch "D" indicates to the generator "G" and/or control system "CS" that the jaw members 110 and 120 are ready to operate in the second bipolar mode of operation. In the second bipolar mode of operation, generator "G" delivers electrosurgical energy to the seal plate 128 and the dissector 90 to dissect the electrosurgically treated tissue. During dissection, the jaw members 110 and 120 may be in either the open or closed position. Moreover, any portion of the dissector 90 may be utilized to dissect the electrosurgically treated tissue.

For example, and in one particular surgical scenario, the jaw members 110 and 120 may be in the open position and the distal tip 93 of the dissector 90 may utilized to dissect the electrosurgically treated tissue. In this instance, the distal tip 93 is positioned adjacent tissue and moved in a direction indicated by directional arrow "M" into the tissue with a force of suitable proportion while simultaneously energizing the seal plate 128 (FIG. 2B).

In another surgical scenario, the jaw members 110 and 120 may be in the open position and seal plate 128 may be utilized to dissect the electrosurgically treated tissue. In this instance, the seal plate 128 is positioned adjacent tissue and moved in a direction indicated by directional arrow "N" across the tissue with a force of suitable proportion while simultaneously energizing the seal plate 128 (FIG. 6).

In yet another surgical scenario, the jaw members 110 and 120 may be, initially, in the open position and seal plate 128 may utilized to dissect the electrosurgically treated tissue. In this instance, the seal plate 128 is positioned adjacent tissue and moved in a direction indicated by directional arrow "O" across the tissue with a force of suitable proportion while simultaneously energizing the seal plate 128 and closing the jaw members 110 and 120 (FIG. 7).

The forceps 10 including the jaw members 110 and 120 overcome some of aforementioned shortcomings of the above-referenced electrosurgical and/or ultrasonic instruments. More particularly, providing the forceps 10 with the jaw member 120 including the seal plate 128 and dissector 90 eliminates the need for a knife blade and components associated therewith to dissect tissue. As can be appreciated, this lowers manufacturing costs of the forceps 10. Moreover, while not discussed in great detail, the shaft 12 may be configured to bend or articulate; this provides a surgeon with greater flexibility with respect to treating and/or dissecting tissue when compared to ultrasonic instruments.

From the foregoing and with reference to the various figure drawings, those skilled in the art will appreciate that certain modifications can also be made to the present disclosure without departing from the scope of the same. For example, in certain embodiments, it may prove useful to have one or both of the seal plates 118 and 128 with a textured or otherwise treated seal surface.

While dissector 90 is described herein as being movable or translatable within the dissector channel 90, it is within the purview of the present disclosure for the dissector 90 to be rigidly or non-movably secured to the seal surface of the seal plate 128 (see FIG. 5). Accordingly, and in this particular instance, the jaw member 120 is configured without a dissector channel 90. In this instance, the dissector 90 will function as previously described. Moreover, the dissector 90 may extend along the length of the jaw member 120 or partially along a length thereof.

In certain embodiments, one or more insulative or non-conductive standoffs 113 (shown in phantom in FIG. 2A) made of any suitable material, e.g., plastic ceramic, etc., may be operably disposed on the seal plate 118. More particularly, the insulative standoff 113 may be operably disposed on the seal surface of the seal plate 118 at a distal end thereof. Insulative standoff 113 may be secured to the seal surface of the seal plate 118 by one or more suitable securement methods, e.g., an adhesive. In the illustrated embodiment, a "pocket" is etched in the seal surface during the manufacture process thereof, a bead of adhesive is placed in the "pocket" and the insulative standoff 113 is positioned therein. Reference is made to commonly-owned U.S. patent application Ser. No. 12/568,199, filed on Sep. 28, 2009, to Brandt et al. for a more detailed description of an etching method that may be utilized with the placement of the insulative standoff 113 on the seal surface of the seal plate 118. Other securement methods are contemplated. The insulative standoff 113 may be configured to contact a distal tip of the seal plate 128 when the jaw members 110 and 120 are in the clamping position such that a gap distance of suitable proportion is present between the seal surface of the seal plate 118 and the seal surface of a seal plate 128 of the jaw member 120. As a result thereof, the jaw members 118 and 128 only contact at their respective tips.

It is contemplated that the generator "G" may be configured to automatically detect when to place the forceps 10 in either the first or second bipolar modes of operation. In this instance, switches 60 may be utilized in a limited capacity or eliminated altogether.

In certain embodiments, a seal plate 118 of the jaw member 110 may include an etched or bored channel that is configured to substantially cover the dissector 90 when the jaw member 110 is moved to the clamping position. For illustrative purposes, a channel 91 of suitable dimension is shown in phantom in FIGS. 4A-5. The channel 91 may be configured to concentrate current densities about the dissector 90 when the forceps 10 is operating in the second bipolar mode of operation and the jaw members 110 and 120 are in the clamping positions.

In certain embodiments, an insulative material 93 may be disposed in vertical registration with the dissector 90, see FIG. 3.

In certain embodiments, the dissector 90 may be configured to operate with jaw members 110 and 120 that are curved or otherwise shaped. In this instance, the dissector 90 may be made from a relatively flexible or resilient conductive material that is configured to conform to the shape of the jaw members 110 and 120. For example, in the instance where the jaw members 110 and 120 are curved and the jaw member 120 includes a dissector channel 101 that is a curved, the dissector 90 may be substantially resilient and configured to bend or flex as the dissector 90 is translated distally and/or proximally.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly for an electrosurgical instrument, comprising:
 a pair of first and second jaw members including respective seal plates adapted to connect to an energy source, at least one of the first and second jaw members movable relative to the other jaw member from an open position, wherein the first and the second jaw members are disposed in spaced relation relative to one another, to a clamping position wherein the first and second jaw members cooperate to grasp tissue therebetween, the first and second jaw members operable in at least two bipolar modes of operation, a first bipolar mode of operation for treating tissue and a second bipolar mode of operation for separating tissue;
 a dissector channel defined longitudinally in the second jaw member, the dissector channel including a bottom surface that is sloped;
 an electrical dissecting member translatable through the dissector channel, the electrical dissecting member in electrical communication with at least one of the seal plates of the first and second jaw members and activatable in the second bipolar mode of operation for separating tissue when the first and second jaw members are in one of the open and clamping positions and tissue is adjacent thereto; wherein the dissector channel is configured to raise the electrical dissecting member above a seal surface of the seal plate of the second jaw member when the electrical dissecting member is translated distally;
 wherein the electrical dissecting member is movable from a partially extended position within the dissector channel where the electrical dissecting member is flush with a seal surface of the seal plate of the second jaw member, to a fully extended position within the dissector channel where the electrical dissecting member is elevated from the seal surface of the seal plate of the second jaw member; and
 wherein when the electrical dissecting member is flush with the seal surface of the seal plate of the second jaw member, the electrical dissecting member and the seal plate of the second jaw member have the same polarity, and when the electrical dissecting member is elevated above the seal surface, the electrical dissecting member and the seal plate of the second jaw member have a different polarity.

2. An end effector assembly according to claim 1, wherein in the first bipolar mode of operation, the electrical dissecting member is flush with the seal surface of the seal plate of the second jaw member and each of the seal plates and the electrical dissecting member are active and electrosurgical energy is transmitted to opposite seal plates, and in the second bipolar mode of operation, the electrical dissecting member is elevated from the seal surface of the seal plate of the second jaw member and the seal plate on the second jaw member is active and electrosurgical energy is transmitted from the second jaw member to the electrical dissecting member.

3. An end effector assembly according to claim 1, wherein the dissector channel extends along the length of the second jaw member to a distal end thereof.

4. An end effector assembly according to claim 1, wherein a protrusion is operably disposed on the second jaw member at a distal end thereof, the protrusion configured to elevate the electrical dissecting member as the electrical dissecting member translates through the dissector channel from the partially extended position to the fully extended position.

5. An end effector assembly according to claim 1, wherein the electrical dissecting member includes a proximal surface having a generally triangular cross-sectional configuration with a tip that is pointed and configured to maximize current densities thereabout.

6. An end effector assembly according to claim 1, wherein the dissector channel is defined by at least two non-conductive interior walls that surround the electrical dissecting member when the electrical dissecting member is translated through the dissector channel.

7. An end effector assembly according to claim 6, wherein the at least two non-conductive interior walls are coated with a non-conductive material.

8. An end effector assembly according to claim 1, wherein the electrical dissecting member is operably coupled to a drive mechanism associated with the electrosurgical instrument.

9. An end effector assembly according to claim 1, wherein the first bipolar mode of operation is configured for one of fusing, sealing, coagulating and fulgurating tissue and the second bipolar mode of operation is configured for one of dissecting, cutting, severing and transecting tissue.

10. An end effector assembly according to claim 1, wherein the width of the seal plate of the first jaw member is smaller than the width of the seal plate of the second jaw member.

* * * * *